(12) United States Patent
Jolley et al.

(10) Patent No.: US 6,596,546 B1
(45) Date of Patent: *Jul. 22, 2003

(54) DETECTION OF ANTIBODIES TO BACTERIAL ANTIGENS BY FLUORESCENCE POLARIZATION

(76) Inventors: Michael E. Jolley, 34469 N. Circle Dr., Round Lake, IL (US) 60030; Klaus H. Nielsen, 75 Richard Dr., Richard Ontario (CA), K0A 2Z0

( * ) Notice: Subject to any disclaimer, the term of this patent is extended or adjusted under 35 U.S.C. 154(b) by 0 days.

This patent is subject to a terminal disclaimer.

(21) Appl. No.: 09/400,798

(22) Filed: Sep. 22, 1999

Related U.S. Application Data

(63) Continuation of application No. 08/520,313, filed on Aug. 28, 1995, now Pat. No. 5,976,820.

(51) Int. Cl.$^7$ .................. G01N 33/533; C07G 17/00; C07H 1/00
(52) U.S. Cl. .................. 436/546; 436/537; 536/1.11; 536/55.1; 536/123; 536/123.1
(58) Field of Search ................. 435/7.32, 7.2, 435/7.92, 968, 537, 546; 436/544, 546; 536/1.11, 4.1, 55.1, 123, 123.1

(56) References Cited

U.S. PATENT DOCUMENTS

| | | | |
|---|---|---|---|
| 4,831,126 A | 5/1989 | Bundle et al. | 536/53 |
| 4,921,878 A | 5/1990 | Rothman et al. | 521/53 |
| 5,006,463 A | * 4/1991 | Cherwonogrodzky et al. | |
| 5,212,298 A | 5/1993 | Rademacher et al. | 536/55.2 |
| 5,445,820 A | 8/1995 | Seidel et al. | 424/237.1 |
| 5,445,935 A | 8/1995 | Royer | 435/6 |
| 5,976,820 A | 11/1999 | Jolley et al. | 435/7.32 |

FOREIGN PATENT DOCUMENTS

| | | |
|---|---|---|
| EP | 0265127 | 4/1988 |
| WO | 9622534 | 7/1996 |

OTHER PUBLICATIONS

Detilleux et al. (Infection and Immunity 1990 vol. 58 pp. 2320–2328).*
Verstreate et al Infection and Immunity vol. 35:3 1982 pp. 979–989.*
Lazar et al. (Molecular & Cellular Biology vol. 8 No. 3 pp. 1247–1252), Mar. 1988.
Burgess et al. (J. of Cell Biology vol. 111 pp. 2129–2138), Nov. 1990.
Salgaller et al. (Cancer Immuno. Immunother.(39) pp. 105–116), 1994.
Toomre et al. (Glycobiology vol. 4 No. 5 pp. 653–663), 1994.
Miller et al. (Am. J. Trop. Med. Hyg. 32(3) pp. 555–564), 1983.
Eichler et al. (Glycoconjugate Journal vol. 8 No. 2 pp. 69–74), 1991.
Venisse et al. (Eur. J. Biochem., vol. 231, pp. 440–447), Jul. 1995.
References in: *Principles and Practice of Immunoassay*, pp. 405–407, second edition, C.P. Price and D.J. Newman, eds., Stockton, 1997.
Jolley, et al. (Clinical Chemistry, 27:7, pp. 1190–1197), 1981.

* cited by examiner

*Primary Examiner*—Patricia A. Duffy
(74) *Attorney, Agent, or Firm*—McDonnell Boehnen Hulbert & Berghoff

(57) ABSTRACT

In a homogeneous immunoassay, fluorophore-conjugated lipopolysaccharide derived bacterial antigens are reacted with antibodies specific for the antigens. Quantitative detection of the formation of an immune complex is obtained by measuring the change in fluorescence polarization after complex formation. The reaction occurs quickly (less than two minutes to equilibrium), and involves the addition of only one reagent to a diluted serum specimen. The absence of a solid phase separation step eliminates false positive results and increases throughput.

8 Claims, 4 Drawing Sheets

Frequency distribution of 9230 known positive (open bars) or negative (closed bars) samples tested for their antibody content against Brucella abortus. Numbers of samples (Y axis) are plotted against a measurement of fluorescence polarization (mP, x axis). The scale of the Y axis has been adjusted to allow observation of the lower number of observations. The numbers above the bard indicate the number of observations for the point. All data was collected using coded samples and data for retested aberrant samples is not included. Using a preliminary cut-off value of 107.2 mP, there were 8 false negative reactions and 24 false positive tests.

FIG. 1

Frequency distribution (same scale as Figure 1) of 8669 serum samples negative for antibody to Brucella abortus (closed bars) and 561 serum samples from animals proven to be infected with B. abortus (open bars). Numbers above bars indicate the number of observations for that point. Data is presented after decoding of samples and retesting false reactions. It is apparent that the cut-off can be lowered to 90mP with a very small decrease in specificity and a gain in sensitivity.

FIG. 2

ROC analysis, plotting % sensitivity (Y axis) against % specificity (X axis) for various cut-off values, after retesting of aberrant samples in the FPIA. The various cut-off values are indicated on the graph. From the data, a cut-off of 90 mP gives a specificity value of 99.96% and a sensitivity value of 99.02%.

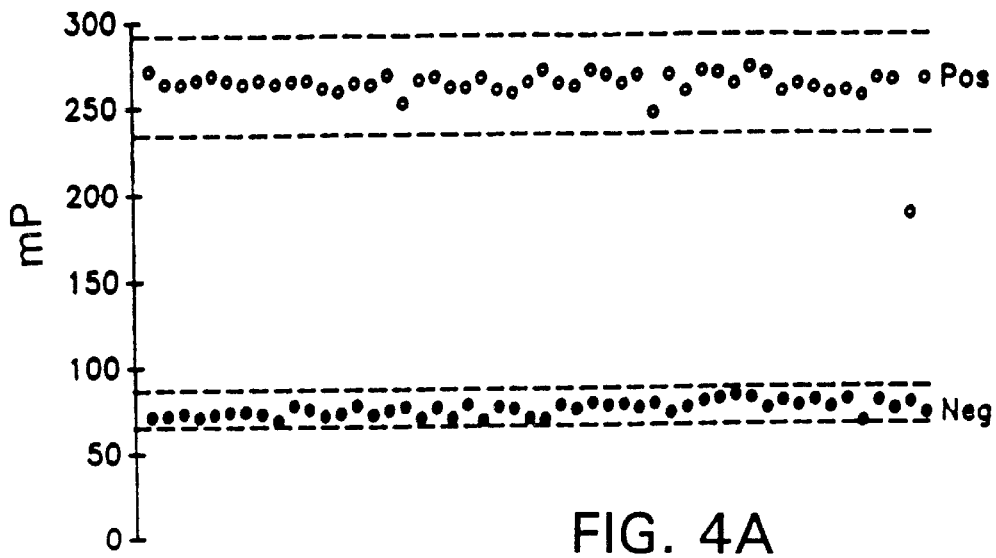

FIG. 4A

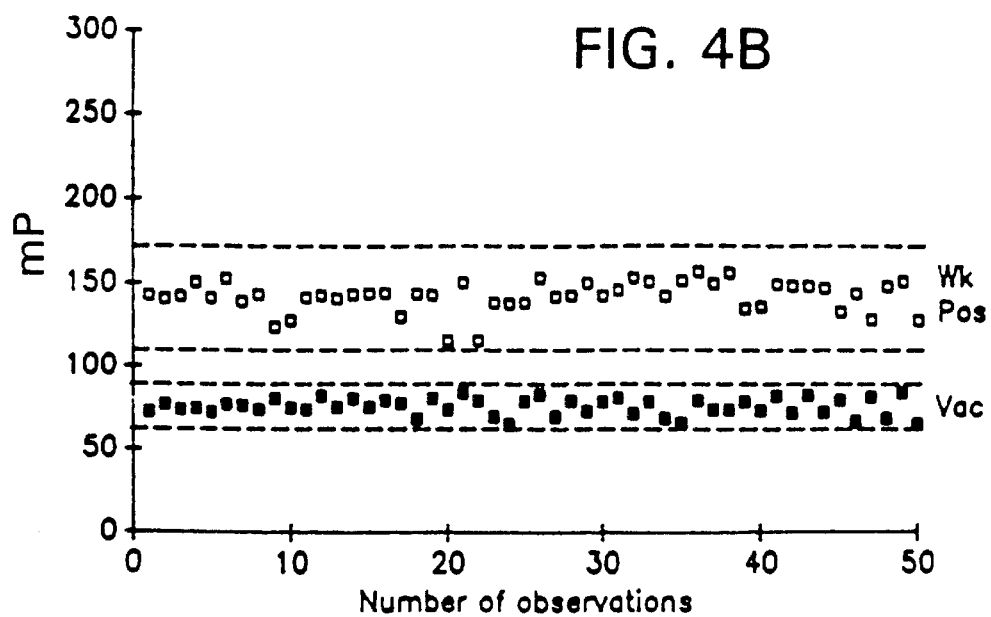

FIG. 4B

Plot of the results obtained with four control sera included with each 100 tests. The controls included a strong positive (open circles), a weak positive (open squares), a negative (closed circles) and serum from a B. abortus strain 19 vaccinated cow (closed squares). The level of positivity (mP, Y axis) is plotted against the number observations for each control. The first 50 observations for each control were selected to eliminate overcrowding of the figure. The broken lines indicate 3 SD on either side of the mean for each set of data.

DETECTION OF ANTIBODIES TO BACTERIAL ANTIGENS BY FLUORESCENCE POLARIZATION

This application is a continuation of U.S. application Ser. No. 08/520,313, filed on Aug. 28, 1995, which issued as U.S. Pat. No. 5,976,820 on Nov. 2, 1999.

BACKGROUND OF THE INVENTION

The presence of a foreign antigenic substance in the body typically gives rise to an immune response. Antibodies specific for the substance are secreted into the blood stream. Diagnostic tests revealing exposure of an animal to an infectious agent rely upon in vitro detection of antibodies specific for antigens expressed by such an infectious agent. In a typical immunoassay, antibodies contained in a serum sample are brought into contact with an antigen preparation. The resulting immune complex is detected in a variety of assay formats including enzyme-linked immunosorbant assay (ELISA), agglutination tests, complement fixation assay, etc.

Many of the assay formats involve adsorption of antigens into a solid phase of such as a plastic bead or particle, a plastic well, or the surface of a plastic or glass tube. The serum containing antigen-specific antibodies are contacted within antigen coated onto solid phase, and washed to remove unreacted serum components. The solid phase-bound antibodies are then detected, for example, by reacting with a species-specific antibody bearing a reporter molecule, washing to remove unreacted reagent, and finally adding a reagent to activate the reporter.

It will be apparent that such assays involve complex binding relationships. There is a tendency for nonspecific antibody to stick to the solid phase, giving rise to false positive tests. Even the best ELISA assays will produce a low level of false positive results. For some of the agglutination assays, specificities of less than 70 percent are obtained.

There have been attempts to eliminate the solid phase artifacts referred to above by detection of analyte antibodies entirely in liquid phase. Termed homogeneous assays, these systems rely upon measuring some changed physico-chemical parameter brought about by molecular interactions. For a review of homogeneous assays systems, see Jenkins, S. H., *J. Immunol. Meth.*, 150: 90 (1992). For applications to macromolecules, see Hosoda, et al.,*J. Immunol. Meth.*, 121: 121 (1989). For review of the theory and practice of fluorescence polarization, a particularly elegant homogeneous system, see M. E. Jolley, *J. Anal. Toxicol.*, 5: 236 (1981).

In the field of infectious disease diagnostics, there is a strong need for assays which have extremely high specificities. In particular, in veterinary diagnostics there are the so-called "program" diseases, which official agencies such as the United States Dept. of Agriculture or Agriculture and Agri-Food Canada administer, and whose eradication is part of their official mandate. The regulations require that a very large number of animals be tested to ensure that new infection is promptly detected and eliminated, and to prove absence of infection.

One of the most important program diseases of livestock is bovine brucellosis. This disease is caused by *Brucella abortus*, a Gram negative bacterium inhabiting the genital tract of cattle. Infected heifers are highly susceptible to abortion, and the economic loss to the cattle industry has been prodigious. Through concerted international efforts to screen for infected animals, and disposal of test positive animals at slaughter, the disease is essentially eradicated in Canada, and the incidence in the U.S. has diminished to less than 150 infected herds. However, Mexico is a persistent reservoir of infection, and movement of cattle in commerce to the U.S. poses a continual risk of new disease. Also, wild animals such as deer and elk are a reservoir of potential new disease in domestic livestock.

As more states become brucellosis-free, and as the overall incidence of disease continues to decline there will be a new emphasis on surveillance programs. In a surveillance situation sensitivity of the assay becomes less important than specificity (so long as the test is sufficiently sensitive to detect a typical reactor). In surveillance testing, false positive tests are troublesome, since any positive test cannot be ignored. For any such positive test, it is official procedure to trace the animal, retest it, and subject it to quarantine. This is extremely costly, and a waste of limited resources.

A large number of cattle in the United States are vaccinated for brucellosis in calfhood, with about 73 percent gaining protective immunity from superinfection with field strains of *B. abortus*. Unfortunately, none of the currently available tests distinguish with high accuracy between true field strain infected animals and vaccinated ones. Specificity is as low as about 50 percent for agglutination tests and up to as high as 97 percent for a C-ELISA assay. In a surveillance program, 3 percent false positives for calfhood vaccinates is a large number in view of the several million cattle tested annually in the U.S. In fact, the high incidence of positive tests for vaccinates, has led some states to repeal their mandatory calfhood vaccination laws, thus depriving the industry of one otherwise valuable tool in the eradication of the disease.

Conventional assays for detection of brucellosis include the ubiquitous agglutination card test in the U.S., the BPAT test in Canada, various versions of a complement fixation test, the Rivanol test, milk ring test (for dairy specimens), and several forms of ELISA including a highly sensitive and specific competitive ELISA developed by Agriculture and Agri-Food Canada. A solid phase bead-based test known as PCFIA is a high throughput automated test used in several official laboratories in the U.S. Many of these tests are commonly used together on the same samples because no one of the conventional, generally available tests detect all the antibody isotypes typically found in field specimens. For a general review of conventional brucellosis tests, see Nielsen, K. and Duncan, J. R., eds., *Animal Brucellosis*, CRC Press: 1990, Chapt. 8.

Brucellosis is but one example of veterinary disease for which a need exists for a sensitive yet highly specific assay approaching 100 percent. Other diseases include tuberculosis (M. bovis), bovine leukosis, leptospirosis, foot and mouth disease (Africa and South America), and salmonellosis.

SUMMARY OF THE INVENTION

In the present invention, a fluorophore-conjugated antigen dissolved freely in solution reacts with antibodies contained in a diluted serum sample to form a immune complex. The immune complex is detected by a change in fluorescence polarization.

It is an object of the invention to provide a homogeneous assay for detecting antibody to selected antigens, thereby eliminating complex, time-consuming adsorption, washing, and detection steps. The assay involves only a single reagent, and a single step reaction in which an immune complex is detectable by a simple fluorescence polarization measurement.

It is a further object of the invention to provide an assay which has extremely high specificity, with less than 0.1 percent down to 0 percent false positive tests, while maintaining a sensitivity of greater than 98 percent.

It is a still further object to provide an assay in which the antigen reagent can be prepared in large reproducible lots of highly uniform composition and performance.

The antigen reagent is also very stable with virtually indefinite lifetime when stored at refrigerated temperatures in the presence of a microbial inhibitor such as sodium azide.

The present method of the invention detects antibodies to bacterial antigens present in fluid comprising combining fluid which may contain antibodies to a bacterial antigen with a fluorophore-conjugated oligosaccharide antigen derived from the lipopolysaccharide antigen derived from the lipopolysaccharide fraction of a bacterial cell wall to form a mixture, incubating the mixture for a time sufficient to form an immune complex, and measuring the extent of formation of the immune complex by comparing the fluorescence polarization after complex formation to an unreacted control value.

The invention provides fluorophore-conjugated antigens comprising oligosaccharides derived from the lipopolysaccharide fraction of a bacterial cell wall. The fluorophore-conjugated oligosaccharide is one embodiment derived from the O-antigen chain of the cell wall lipopolysaccharide fraction from bacteria, such as Gram negative bacteria, having us O-antigen chain.

The invention similarly comprises a homogeneous immunoassay in which antibodies to an antigen are reacted with an antigen to form an immune complex, the improvement to previous technology being a fluorophore-conjugated oligosaccharide antigen of bacterial cell wall forming a fluorescence polarization detectable immune complex with antibodies specific thereto.

The fluorophore-conjugated oligosaccharide antigens may be derived from any bacterium having a lipopolysaccharide cell wall fraction, as antigens derived from Gram negative bacteria such as B. abortus, Leptospira spp, or Salmonella spp. The fluorophore will have an emission life of 1 to 10 nanoseconds, and its emission may vary over a wave length of 400 to 800 nanometers. In the present invention, the fluorophore fluorescein is efficacious.

BRIEF DESCRIPTION OF THE DRAWINGS

FIG. 1 is a frequency distribution of positive and negative serum samples from a study of 9230 known positive or negative sera.

FIG. 2 is a frequency distribution of 8669 negative sera and 561 positive sera from culture confirmed infected cattle.

FIGS. 4A and 4B are plots of four control sera included with each 100 tests.

DETAILED DESCRIPTION OF THE PREFERRED EMBODIMENT

Figure 3:
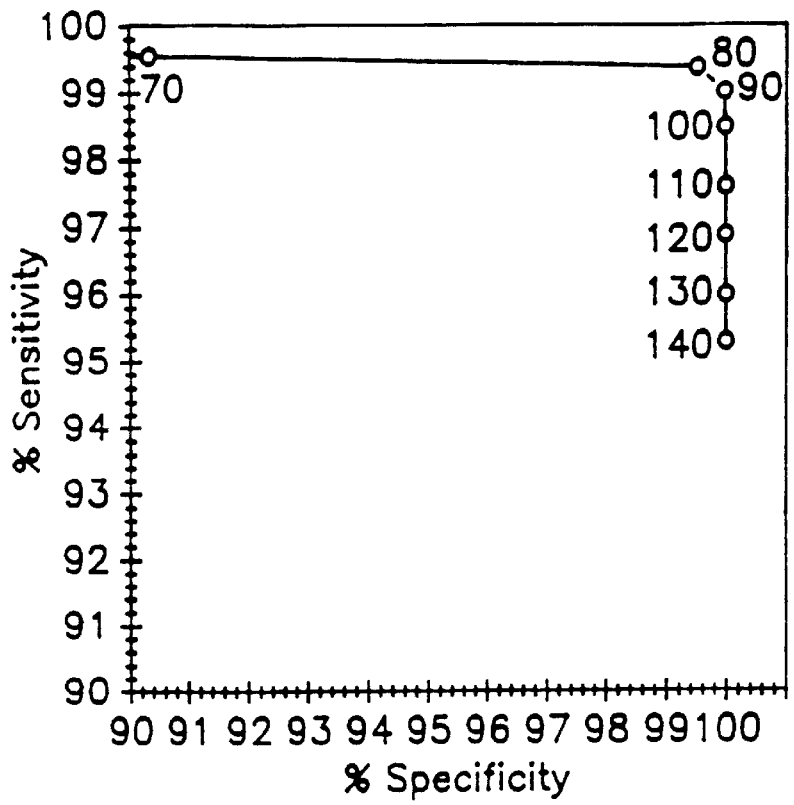
FIG. 3 is a rectilinear plot of sensitivity vs. specificity.

The assay of the present invention takes advantage of the well-known highly specific binding of antibodies to their corresponding antigens. When a bacterium invades an immunocompetent animal, certain structural/chemical moieties present on its surface are recognized as foreign by the immune system. Secretion of antigen-specific antibody ensues. The population of antibodies is generally very heterogenous, with individual antibody molecules recognizing and binding different epitopes. In preparing useful antigens as targets in immunoassays, it is therefore important to select antigenic structures which contain the immunodominant epitopes, so that there is a strong likelihood of correctly identifying the largest possible number of positive sera.

Gram negative bacteria have cell walls that characteristically contain a diverse family of specialized glycolipids in which the saccharide forms repeating O-antigen chains, attached through non-repeating core glycan to lipid A, which is integrated into the outer membrane. In Salmonella, as a typical model system, synthesis of the entire core sequence occurs by glycosyl transfers from sugar nucleotides, with addition at the nonreducing terminal and catalysis by glycosyl transferases. The O-antigens generally act as surface antigens, and contain many of the immunodominant epitopes. These antigens also, when shed, behave as bacterial toxins. The O-antigen chains are synthesized separately as modular glycans. The modules are spliced together before becoming linked to the core sequence.

In many bacterial species, the O-antigen chains are simpler than in Salmonella. In one species of great interest from a diagnostics standpoint, B. abortus, the O-antigen polysaccharides have 1–2 linked 4,6-dideoxy-4-formamido-alpha-D-mannopyranosyl repeating units. The O-polysaccharide is extractible as an approximately 15,000–30,000 molecular weight molecule. There are many extraction methods for obtaining purified O-chain antigen reported in the literature for Gram negative bacteria generally. For Brucella abortus or Yersinia enterocolitica 0:9, phenol-water extraction, followed by dialysis and centrifugation may be used, as described in U.S. Pat. No. 4,831,126 or 5,006,463, hereby incorporated by reference. This method has been modified somewhat to improve purity and yield, as described in Nielsen, et al., Am. J. Vet Res. 50: 5 (1989).

In extracting and purifying a lipid-free arabinomannan antigen preparation from Mycobacterium species, the lipid fraction may be removed by extraction with acetone, ether-methanol, and chloroform successively, and then releasing the antigen fraction by alkaline hydrolysis. Further purification may be effected through ion exchange chromatography and gel filtration.

Extraction and characterization procedures for Gram negative bacterial polysaccharide antigens are well-known in the literature. Satisfactory methods for the preparation of the intact polysaccharide antigens of the present invention are available for all significant Gram negative pathogens, or may be readily adapted from existing methods. Libraries of the general structural characteristics of families of polysaccharides of diverse origin and of the antigens of pathogens in particular are available. For example, see Griffith, et al., "Type-specific carbohydrate antigens of pathogenic bacteria," Carbohydrate Polymers, vol. 14, p.339. Also a detailed review is available in Vols. 235 and 236 of Methods in Enzymoloy, Academic Press: 1988. Another source of protocols for extraction of antigenic polysaccharides from bacteria for extraction of antigenic polysaccharides from bacteria is Methods in Carbohydrate Chemistry, vols. 4, 8, 28, 50, 179, and 230 (Academic Press: various years).

In preparing the antigens of the present invention, it is necessary to reduce the antigen to a small size, but not so small as to lose its immunodominant epitopes. In the case of many of the O-antigen repeating subunits, the length of polymer estimated to fill an antibody combining site is on the order of 4–6 sugar residues. The O-antigen may be conveniently reduced in size by several methods, including acid or base hydrolysis, enzymes, oxidative or reductive processes, or by techniques known to result in selective cleavage at specific glycosidic linkages. The general protocol for preparation of bacteria-derived polysaccharide antigen fragments useful in the present invention is:

(1) Separate polysaccharide antigen from other cellular components. (Conventional method by one of the published techniques).

(2) Selective precipitation of the polysaccharides or of their salts or complexes.

(3) Resolubilization and optional chromatographic separation based on charge, size, or ligand affinity, or combination thereof.

(4) Partial hydrolysis to reduce the size (or by the specific cleavage or oxidative/reductive methods referred to above). Base hydrolysis in 0.1 to 1.5N NaCl is preferred for any of the bacterial O-antigens.

(5) Labeling with a fluorescent moiety.

(6) Purification by gel filtration (size) and ion exchange chromatography (separation by charge).

It will be recognized that the conditions of extraction and fragmentation of the O-antigens will differ somewhat from the one genus or species of Gram negative bacteria to another. While the above general protocol is generally applicable to any given bacterium, there will be variations in procedure. Some experimentation will be necessary to achieve a satisfactory antigen in a given situation. The ultimate test is performance of the labeled antigen against actual blinded serum panels of known infected and disease-free animals. Use of monoclonal antibodies to screen suitable tracers is remarkably, and surprisingly, unreliable. However, if the general protocol set forth herein is followed for the fluorescence polarization-based assay disclosed hereinafter, a suitable reagent can be identified with very limited experimentation. For example, complete identification and preliminary validation of a fluorescein-conjugated reagent obtained from an alkali hydrolysate of *B. abortus* O-antigen was developed in about three weeks of testing. The generic Mycobacterium arabinomannan-derived reagent took even less time to develop. In general, a suitable antigen will produce greater than 99 percent and upwardly 100 percent specificity for the target organism, with greater than 98 percent sensitivity utilizing sufficient positive and negative sera to give statistical significance levels having p values of less than 0.05.

The chemistry of carbohydrate fluorescence labeling is very complex, and the number of fluorescent derivatives possible is virtually unlimited. For a detailed review, see Ginsburg, V., "Complex Carbohydrates", in *Methods of Enzymology*, vol. 138, Academic Press: 1987. In the Examples, fluorescein was conjugated to the O-antigen through coupling fluorescein isothiocyanate. Many other coupling mechanisms are known in the art. Some aspects of the coupling rationale are as follows:

Most carbohydrates do not possess amino or carboxyl groups. The only groups available for attachment of fluorophores are hydroxyl groups and the terminal reducing aldehyde group. Therefore, conventional protein labeling reagents may not be appropriate for the labeling of carbohydrates with fluorochromes. Fluorescein isothiocyanate (FITC), however, will react slowly with hydroxyl groups. Indeed, FITC-labeled dextran and FITC-labeled inulin have been used for many years in permeability studies in cells and tissues [Rutili, G. and Arfors, K. E., *Microvasc. Res.* 12:221 (1976); Sohtell, M., et al., *Acta Physiol. Scand.* 119:313 (1983)].

Dichlorotriazinyl-aminofluorescein (DTAF) [Blakeslee, D., *J. Immunol. Methods* 13:305 (1976)]; [Blakeslee, D., *J. Immunol. Methods* 17:361 (1977)] reacts readily with alcohols in the presence of water [Chayen, R., et al., *Anal. Biochem.* 39:533 (1971)]; DeBelder, A.N., et al., *Carbohyd. Res.* 30:375 (1973)]. DTAF was used to successfully label the 6-position of the sugar moiety in muramyl depeptide when all efforts to employ FITC had failed [Hiebert, C. K., et al., *J. Med. Chem.* 26:1729 (1983)].

Reductive amination of the terminal reducing sugar residue has been used to label carbohydrates with a variety of fluorophores including pyridylamine [Hase, S., et al., *J. Biochem.* 95:197 (1984)] and fluoresceinyl-ethylene diamine [Baynes, J. W., et al., *Anal. Biochem.* 170:382 (1988)]. The carbohydrate and fluorophore, possessing an amino group, are mixed together and the Schiff base formed is reduced to a stable amino linkage with sodium cyanoborohyride. Alternatively the terminal aldehyde may be converted to an amino group by incubation with ammonium bicarbonate and then reacted with fluorophores such as carboxyfluorescein or dansyl chloride [Manger, I. D., et al., *Biochemistry* 31:10724 (1992)]

Aldehydes may be generated in carbohydrates by periodate oxidation of vicinal hydroxyl groups [Rothfus, J. A. and Smith, E. L., *J. Biol. Chem.* 238:1402 (1963)]. RNA was labeled at its 3'-terminal ribose in this way with 5[[[2 (carbohydrazino)methyl]thio]acetyl]-aminofluorescein [Janiak, F., et al., *Biochemistry* 31:5830 (1992)] and with rhodamine and fluorescein thiosemicarbazide [Bauman, J. G., *J. Histochem. Cytochem.* 29:227 (1981)]. The carbohydrate moiety of human alpha thrombin was labeled with aminoethyl and aminohexyl thioureal fluorescein [Carney, D. H., *J. Supramol. Struc.* 13:467 (1980)] and the cercarial glycocalyx of *Schistosoma mansoni* by fluorescein semicarbazide [Samuelson, J. C. and Caulfield, J. P., *J. Cell Biol.* 100:1423 (1985)].

Aldehydes may be generated and labeled at specific residues by combining enzymatic and chemical reactions. For example, galactose oxidase may be used to form the C-6 aldehyde on terminal D-galactose or N-acetyl-D-galactosamine residues [Avigad, E., et al., *J. Biol. Chem.* 237:2736 (1962)]. The same enzyme, in combination with neuraminidase, was used to modify galactosyl residues penultimate to sialic acids and subsequently reacted with fluorescein β-alanine hydrazide [Wilchek, M. and Bayer, E. A., *Methods Enzymol.* 138:429 (1987)].

The choice of fluorophore is to a large extent a matter of convenience once a coupling chemistry has been selected. Virtually any fluorophore having a fluorescence life of between 1 and 10 nanoseconds, preferably 4 to 7 nanoseconds, and having a wavelength of 400 to 800 nanometers will have efficacy in the present invention. The choice of fluorophores will influence the configuration and requirements of the optics of the instrument used to read the assays. It will also impact the optics technology utilized. For a detailed listing and discussion of a variety of interesting, commercially available fluorophores, see *Handbook of Fluorescent Probes and Research Chemicals*, ed. Karen Larison, by Richard P. Haugland, Ph.D., 5th ed., 1992, published by Molecular Probes, Inc. Preferred fluorophores in the labeled antigens of the present invention are fluorescein, rhodamine, BODIPY™, Texas Red™ and Lucifer yellow. Fluorescein is most preferred for its convenience in screening O-antigen fragments for good assay candidates.

In the assays of the present invention, the fluorophore-conjugated oligosaccharide antigens are mixed with a serum sample diluted in a conventionally buffered solution, allowed to react for 1 to 3 minutes, and read in a fluorescence polarization instrument. Typically a background value is obtained prior to addition of the antigen reagent. The assay is homogeneous, in that no further steps are required, as in heterogeneous assays in which antibody contained in the sample must be bound to antigen coated onto a solid surface, with subsequent washing and detection steps. The assay is carried out at temperatures of 15° C. to 37° C., but the assay may be carried out under any temperature and reaction conditions which permit specific immune complex formation.

In fluorescence polarization (FP), a molecule conjugated to a fluorophore is present in solution. The molecular rotation of the molecule in solution is a function of its size and the viscosity of the solution. If the fluorophore-conjugated molecule is relatively small compared to its size when bound to a larger molecule, such as an antibody, the fluorescence emitted by such small molecule will be relatively less polarized than when it is bound. This is because the complaced ligand target molecule is at relatively large, and rotates more slowly. Hence, more of the emitted light is directed in one geometric plane, and the fluorescence polarization value increases. The application of FP to quantitative detection of drugs in an immunoassay is disclosed in U.S. Pat. No. 5,427,960, hereby incorporated by reference. For reference to some of the key developmental papers in the literature of this technology, see Perrin, F., *J. Phys. Radium* 7:390–401 (1926), Weber, G., *Adv. Protein Chem.* 8:415–59 (1953), Dandliker, W. B. and Feigen, G. A., *Biochem. Biophys. Res. Commun.* 5:299–304 (1961), Dandliker, W. B. and de Saussure, V. A., *Immunochemistry* 7:799–828 (1970), Dandliker, W. B., et al., *Immunochemistry* 10:219–27 (1973), Jolley, M. E., *J. Anal. Toxicol.* 5:236–240 (1981).

FP has the following important characteristics: it detects change in size of molecules, it detects change in viscosity of the medium, it may be used to detect and measure binding of small molecules to big molecules. In addition, it has broad application in detection and measurement of the conversion of large molecules to small molecules. The FP assay is homogeneous, (reactions take seconds to minutes), utilizes stable reagents, (no enzymes, substrates or radioisotopes) and is highly automatable, (single incubation, a single reagent is possible, and no washing steps are required).

Further advantages of the antigens and immunoassays of the present invention will be apparent from the Examples which follow:

EXAMPLE 1

Preparation of Brucella Tracer. O-polysaccharide (3.0 mg) was dissolved in 600 μL of 0.1 N NaOH and incubated at 37° C. for 1 hour. 300 μL of a freshly prepared solution of FITC isomer I (Sigma Cat. No. F-7250) in DMSO (Mallinkrodt Cat. No. 4948) 100 mg/mL) was added, mixed well, and incubated 1 hour at 37° C. The reaction mixture was then applied to a DEAE-Sephadex A25 (Signa Cat. No. A25-120) column (20 mL packed volume in a 20 mL syringe, equilibrated with 0.01 M phosphate buffer pH 7.4). The column was eluted with 0.01 M phosphate buffer, pH 7.4. Two fractions were collected. The first was buffer (7 mL) and the second, a bright green fluorescent fraction (tracer I10-1; 7 mL). The elution buffer was then changed to 0.1 M phosphate, pH 7.4. Two fractions were collected. The first was buffer (10 mL) and the second, a bright green fluorescent fraction (tracer I10-2; 25 mL). The latter fraction contained the best tracer.

TABLE 1

| Tracer | μl/assay | mP − ve | mP Strong + ve | mP Weak + ve 16469 |
|--------|----------|---------|----------------|--------------------|
| I10-1  | 0.5      | 84.8    | 176.4          | 110.4              |
| I10-2  | 1.5      | 80.9    | 225.7          | 138.6              |

Therefore, the yield is approximately 5000 assays per mg.

EXAMPLE 2

Brucellosis Assay. The following is the general protocol for performing the *B. abortus* assays in the examples which follow.

1. All steps of the assay were performed at ambient temperature.
2. To 2 mL of phosphate buffered saline, containing 0.05% lithium dodecyl sulfate and 0.1% sodium azide (PBSA), was added 20 μL of serum sample.
3. A blank subtraction was performed on an FPM-1™ (Jolley Consulting and Research Inc., Grayslake, Ill.).
4. Tracer (10 μL, diluted in PBSA to yield approximately 1.5 nM fluorescein equivalents in the final assay mixture, was added.
5. After an incubation of greater than 2 minutes the fluorescence polarization of the tracer was determined.

EXAMPLE 3

Extraction and purification of Lipid-free Arabinomannan Antigens of *Mycobacterium paratuberculosis* or *Mycobacterium bovis*. The protocol for preparation of the antigen is as follows. Also refer to Misaki, A., et al., *J. Biochem.* 82:701 (1977) and Sugden E. A., et al., *Infect. Immun.* 55:762 (1987).

1. Grow a laboratory-adapted strain of *M. paratuberculosis* (Animal Diseases Research Institute strain V) in modified Long's synthetic medium [Landi, S. *Bull Internat. Union against Tuberc* 49:112 (1973)] for 3 months at 37° C. Alternatively, grow *M. bovis AN*-4 in modified Reid's synthetic medium [Angus, R. D., *J. Biol. Stand.* 6:221 (1978)] for 10 weeks at 37° C.
2. Kill *M. paratuberculosis* in 3% phenol and kill *M. bovis AN*-5 by autoclaving at 121° C. for 45 minutes.
3. Wash *M. paratuberculosis* or *M. bovis* killed bacilli with water and drain dry. Store frozen at 20° C.
4. Extract lipid from bacilli at 4–7° C. with acetone, ether-ethanol (2:1), and chloroform successively for 4 hours for each solvent, and with chloroform-methanol (2:1) for 18 hours (i.e., overnight). Wash with acetone for 1 hour to displace the chloroform-methanol. Use enough solvent volume in each case to give approximately 10 fold that of the settled bacillary mass. After each extraction filter through Whatman No. 1 filter paper. Perform in fume hood.
5. Air-dry bacilli in a fume hood and store at 4–7° C. in a polyethylene container.
6. Extract 100 g of dried bacilli with 100 ml of 0.5 N NaOH at 70° C. for 8 hours in a glass beaker placed over a submersible magnetic stirrer in a water bath. Cover lightly with parafilm and purge with a low stream of N2 gas from a compressed tank. Stir constantly.
7. Cool extract and neutralize to pH 7.0–7.5 with glacial acetic acid using a pH meter at room temperature.

8. Centrifuge extract at 30,000×g for 30 minutes at 5° C. and collect extract supernatant. Discard the pellet.
9. Dialyse extract supernatant against tap water for 2 days in 3,500 Molecular Weight Cutoff dialysis tubing, and for 2 days with 2 volumes of each with at least a 20 fold excess of distilled water for each volume.
10. Add 100% Ethanol with stirring in a glass beaker at room temperature to give a final concentration of 30% ethanol. Centrifuge at low speed at room temperature and collect supernatant. Discard precipitate.
11. Add a further quantity of 100% ethanol with stirring in a glass beaker at room temperature to give a final concentration of 66% ethanol. Centrifuge at low speed at room temperature and collect supernatant. Discard precipitate.
12. Add a further quantity of 100% ethanol with stirring in a glass beaker at room temperature to give a final concentration of 80% ethanol. Centrifuge at low speed at room temperature and collect supernatant.
13. Suspend the 80% ethanol gummy precipitate in approximately 100 ml water and dialyse for 2 days with 2 volumes of each with at least a 20 fold excess of distilled water. Lyophilize and store in a desiccator at 4–7° C.
14. Resuspend in a minimum volume of 1.0M NaCl, 0.1M Tris, pH 8.0, 0.02k NaN$_3$ (Tris-NaCl) and stir to completely dissolve. Estimate carbohydrate concentration by the phenol-sulfuric acid test using 10 mg % glucose in Tris-NaCl as a standard. To 0.2 ml sample, add 0.2 ml 4.5% phenol and mix well. Add 1 ml of concentrated sulfuric acid rapidly to the mixture. After mixing further and cooling, read at 490 nm in a spectrophotometer. The recovery of carbohydrate in the 80% gummy precipitate was approximately 10 mg/g (on a dry-weight basis) of dried solvent extracted bacilli.
15. Apply up to 1000 mg of 80% ethanol precipitated carbohydrate material in no more than 30 ml to a 5.0×89.5 cm column of Sephacryl S-200 (Pharmacia Fine Chemicals) pre-equilibrated with Tris-NaCl and run at 81.9 ml/h and 4° C., collecting 25.2 ml fractions. Monitor fractions with the phenol-sulfuric acid test (step 14) and collect pools (e.g. fractions 36–48, 49–60, 61–70). The later fractions have lower molecular weights. Dialyse with tap and distilled water as before (step 9) and lyophilize. Store at 4–7° C. in a desiccator.
16. Chromatograph selected pools reconstituted in 30 ml of 0.05M Tris, pH 8.0, 0.02% NaN$_3$ (Tris) on a 1.6× 69.5 cm column of DEAE-Sephacel A25 (Pharmacia) pre-equilibrated with Tris, and run at 25 ml/h at 5° C., collecting 14 ml fractions. Elute with 300 ml of Tris and collect the non-retained carbohydrate material, monitoring with the phenol-sulfuric acid test (step 14).
17. Dialyse the pooled non-retained carbohydrate from DEAE-Sephacel chromatography as before (step 9), determine the carbohydrate concentration with the phenol-sulfuric acid test (step 14) and lyophilize in 10 mg aliquots (Note: 10 mg vials are based on the phenol-sulfuric acid definition of mass and not on a dry-weight basis). Store at 4–7° C. in a desiccator.
18. The recovery of the Sephacryl S-200 pool of 36–48 (step 15) from DEAE Sephacel (step 16) is approximately 5 mg/g (on a dry-weight basis) of dried solvent extracted bacilli and is defined as alkaline-extracted lipid-free arabinomannan.

EXAMPLE 4

Preparation of Mycobacterium Tracer

1. To each of two vials of lyophilized arabinomannan in 5 ml serum bottles labeled M PARA STR V AZ-AM ANTIGEN 10 mg 20-11-86 add 1 ml of 0.1 N NaOH freshly prepared. Stopper with grey lyophilization stoppers and incubate in a 37° C. incubator oven for 1 hour.
2. Add the two 1 ml aliquots of arabinomannan in 0.1 N. NaOH to a 16×100 mm disposable (Baxter T1290-6) test tube containing 2.2 mg of freshly weighed 5-Fluorescein Isothiocyanate (Eastman Kodak Cat. No. C10868, lot H3F, Dye content 76%, 11/73). Incubate 1 hour at 37° C.
3. Apply reaction mixture to a 29×1 cm column of Sephadex G-25 (which had been slurried and had had the fines removed) pre-equilibrated with 0.1M solidum phosphate pH 7.0. Flow rate was approximately 0.25 ml/ml. Collect 1 ml fractions and monitor at 492 nm.

Observed clear separation of leading yellow void peak from following yellow orangish material.

4. Apply Sephadex G-25 pooled fractions 10-14 to an 18×1 cm column of DEAE-Sephadex A25 equilibrated with 0.1M sodium phosphate pH 7.0 and elute with same buffer at 0.25 ml/min. Collect 1 ml fractions and collect pools 11-15 (tracer 3), 16-20 (tracer 1), and 21-15 (tracer 2).

EXAMPLE 5

Monoclonal antibodies cannot be used to screen tracers for reactivity to antibodies generated by natural infection in bovines, as shown in Table 2. Tracer 94082502, for example, reacts strongly with mAB ST9, specific for the o-polysaccharide from *B. abortus*. However, on testing against a panel of five known positive bovine sera, it failed to detect two of them (POS1, POS3) and reacted weakly with a strong positive (POS4). Tracer 9408201, however, reacted strongly with all of these samples, but poorly with mAb YST9.

EXAMPLE 6

A fluorescence polarization assay for the detection of antibodies to *M. paratuberculosis* and *M. bovis* was compared to a reference ELISA (ADRI). Results compared favorably with some exceptions as seen in Table 3. Negative samples 54 was positive in ELISA (high cutoff) but negative by FP. Positive samples 52C8, 27A9 and 194F9 were negative by ELISA (high cutoff) and positive by FP (105 mP cutoff). Using the low cutoff ELISA was positive on positive samples 36-33 and FP was negative; samples 52C8 and 27A9 became positive. However, using the low cutoff ELISA, negative samples 103E9, 106E9, 54 and 56 became positive.

TABLE 3

| ID | STATUS | ELISA | CO | CO | FP | NEG CT | POS CT |
|---|---|---|---|---|---|---|---|
| 103E9 | M PTB− | 0.198 | POS | NEG | 103.3 | 98 | 269.5 |
| 106E9 | M PTB− | 0.186 | POS | NEG | 104.9 | 98 | 269.5 |
| 54 | M BOV− | 0.26 | POS | POS | 101.6 | 98 | 269.5 |
| 56 | M BOV− | 0.254 | POS | NEG | 101.2 | 98 | 269.5 |
| 34A9 | M PTB+ | 0.938 | POS | POS | 139.4 | 100.7 | 273.5 |
| 41A9 | M PTB+ | 0.572 | POS | POS | 125.9 | 100.7 | 273.5 |

TABLE 3-continued

| ID | STATUS | ELISA | CO | CO | FP | NEG CT | POS CT |
|---|---|---|---|---|---|---|---|
| 27A9 | M PTB+ | 0.232 | POS | NEG | 118.7 | 100.7 | 273.5 |
| 52C8 | M PTB+ | 0.228 | POS | NEG | 111.7 | 100.7 | 273.5 |
| 194F9 | M PTB+ | 0.097 | NEG | NEG | 1205.3 | 100.7 | 273.5 |
| 57C8 | M PTB+ | 0.093 | NEG | NEG | 103.4 | 100.7 | 273.5 |
| 34-535082 | M BOV+ | 1.973 | POS | POS | 273.5 | 100.7 | 273.5 |
| 34-135080 | M BOV+ | 1.763 | POS | POS | 124.0 | 100.7 | 273.5 |
| 36-33 | M BOV+ | 0.19 | POS | NEG | 102.5 | 100.7 | 273.5 |
| 15-67 | M BOV+ | 0.151 | NEG | NEG | 102.9 | 100.7 | 273.5 |
| 34-335081 | M BOV+ | 0.101 | NEG | NEG | 101.7 | 100.7 | 273.5 |
| 15-48 | M BOV+ | 0.091 | NEG | NEG | 104.6 | 100.7 | 273.5 |

EXAMPLE 7

The fluorescence polarization assay for *B. abortus* antibodies was tested twice on a panel of bovine serum samples which gave disparate results on reference assays. See Table 4.

The FP results were consistent with the test interpretations on all samples. Note especially samples OW-1 (CARD false negative), IC88 (CARD and CF false positive), TO-1® (CARD false positive), and CV25 (CARD false positive).

EXAMPLE 8

In a blind study, a total of 9480 bovine sera were tested in addition to sets of four controls, included with every 100 samples tested. The controls were a strong positive, a weak positive, a negative and a serum derived from a *B. abortus* strain 19 vaccinated animal. Test sera included 8669 sera from Canadian cattle, previously tested negative by routine serological tests, 561 sera from animals from with *B. abortus* has been isolated, either from tissues or milk and 250 sera from animals vaccinated with *B. abortus* strain 19 at various times previously. One lot of O-polysaccharide tracer was used for all tests, and was prepared as disclosed in Example 1.

Assay sensitivity and specificity for the FPIA before and after decoding of the serum samples are as follows. Using a preliminary cutoff of 107.2 mP, the point estimates of sensitivity and the specificity of the FPA after initially testing all samples were 98.2+/−1.1% and 99.8+/−0.09%, respectively. After decoding and retesting false positive and false negative samples, the values increased to 98.5+/−1% and 100%, respectively.

FIGS. 1 and 2 represent histograms of the distribution of results obtained with the positive and negative sera in the FPA before and after decoding of the samples. While the cutoff from FIG. 1 is difficult to determine because of the overlap between positive and negative samples in the 90 to 140 mP region, it is clear that the cutoff should be above 100 mP and a 107.2 value as calculated using the 100th percentile of the negative sera is not unreasonable. From FIG. 2, however, after retesting 24 false positive samples, it is apparent that the cutoff should be set at a lower level. If a value of 90 mP is selected, three false negative results and one false positive are evident. These findings were confirmed using ROC analysis (FIG. 3). Thus, if a cutoff of 90 mP is selected, the sensitivity and specificity values are 99.02 and 99.96%, respectively.

Of the eight serum samples from animals with confirmed brucellosis that remained negative in the FPIA, 1 originated from a cow infected with the vaccine strain of *B. abortus* and was negative on all serological tests. Of the remaining, three animals were infected with field strains of *B. abortus* and two were serologically negative on all tests while two sera were positive in all tests including the PFIA. In addition to these 8 serum samples, a sample from another strain 19 infected animal was positive in the FPA but negative in other serological tests. These data are presented in Table 5.

The four control sera, a strong positive, a weak positive, a negative and a serum from a vaccinated animal, included in each 100 samples tested were plotted in FIGS. 4A, B, C and D. Each point represents an individual determination. The upper and lower lines for each set of points indicate +/−2 standard deviations of the mean. Of the sera obtained from *B. abortus* strain 19 vaccinated cattle, 2 gave positive reactions in the FPIA using cutoff of 90 mP, giving a point specificity value of 99.2%. For comparison, the specificity in the BPAT was 48.6%, the CFT was 49.0% (87 of 250 sera were anticomplementary and no diagnosis could be made), the I-ELISA was 56.3% and the C-ELISA was 97.2%. These data are presented in Table 6.

TABLE 5

Results obtained in various tests with serum samples that gave preliminary false negative reactions in the FPA.

| Serum | Culture[1] | BPAT[2] | CFT[3] | I-ELISA[4] | C-ELISA[5] | FPA[6] |
|---|---|---|---|---|---|---|
| 1 | FS | − | − | .290 | 14 | 77.3 |
| 2 | FS | + | | .750 | 36 | 94.7 |
| 3 | FS | − | − | .115 | 13 | 81.3 |
| 4 | FS | + | | .950 | 80 | 232.8 |
| 5 | S19 | − | − | .310 | 6 | 77.9 |
| 6 | S19 | − | − | .286 | 14 | 93.8 |

[2]Results of bacteriological culture of <u>*B.abortus*</u> strain 19 (S19) or field strain (FS).
[2]Buffered plate antigen result, either positive or negative.
[3]Complement fixation test titer (reciprocal).
[4]Optical density reading in the indirect enzyme immunoassay. A reading of 0.460 is considered positive.
[5]Percent inhibition in the competitive enzyme immunoassay. Inhibition of 30% or greater is considered positive.
[6]Results in fluorescence polarization assay. A reading of 90 mP or higher is considered positive.

TABLE 6

Point specificity values of serological tests used to evaluate the antibody content in sera from 250 cattle vaccinated with <u>*B.abortus*</u> strain 19 at various times previously. All sera were positive in one or more of the assays.

| Test | Specificity % | Cutoff Used |
|---|---|---|
| BPAT | 48.6 | + or − |
| CFT | 49.0 | Reaction at 1:5[1] |
| I-ELISA | 56.3 | 46% positivity[2] |
| C-ELISA | 97.7 | 30% inhibition[2] |
| FPIA | 99.2 | 90 Mp |

[1]87 sera were anticomplementary and no diagnosis could be made.
[2]compared to a known reaction.

What is claimed is:

1. A purified fluorophore-conjugated bacterial antigen comprising an oligosaccharide fragment of an O-antigen polysaccharide from the lipopolysaccharide of a Gram negative bacterial cell wall and a fluorophore conjugated to said oligosaccharide fragment, wherein said fluorphore-conjugated oligosaccharide fragment is able to bind to antibodies specific to said bacterial antigen and said binding produces a detectable change in fluorescence polarization of the flurophore-conjugated oligosaccharide conjugate.

2. The fluorophore-conjugated oligosaccharide fragment of claim 1, wherein the oligosaccharide fragment is prepared by partial hybrolysis of said O-antigen polysaccharide.

3. The fluorophore-conjugated oligosaccharide fragment of claim 1, wherein the oligosaccharide fragment is prepared from said O-antigen polysaccharide by an enzymatic process.

4. The fluorophore-conjugated oligosaccharide fragment of claim 1, wherein the oligosaccharide fragment is prepared from said O-antigen polysaccharide by an oxidative process.

5. The fluorophore-conjugated oligosaccharide fragment of claim 1, wherein the oligosaccharide fragment is prepared from said O-antigen polysaccharide by a reductive process.

6. The fluorophore-conjugated oligosaccharide fragment of claim 1, wherein the oligosaccharide fragment is prepared by selective cleavage of said O-antigen polysaccharide.

7. The fluorophore-conjugated oligosaccharide fragment of claim 1, wherein the fluorophore is selected from the group consisting of fluorescein, rhodamine, lucifer yellow, BODIPY™(4,4-difluoro-4-bora-3a,4a-diaza-s-indacene) and TEXAS RED™ (sulforhodamine 101 acid chloride).

8. The fluorophore-conjugated oligosaccharide fragment of claim 1, wherein the oligosaccharide fragment has a molecular weight ranging from 1,000 to 30,000 daltons.

* * * * *